(12) United States Patent
Graham

(10) Patent No.: US 6,910,883 B2
(45) Date of Patent: Jun. 28, 2005

(54) ORTHODONTIC BRACKET CLEANER

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 175 days.

(21) Appl. No.: 10/384,688

(22) Filed: Mar. 11, 2003

(65) Prior Publication Data

US 2004/0180307 A1 Sep. 16, 2004

(51) Int. Cl.$^7$ ............................... A61C 3/00; A61C 3/03
(52) U.S. Cl. ............................ 433/3; 433/118; 132/322
(58) Field of Search ........................... 433/3, 118–124; 132/322

(56) References Cited

U.S. PATENT DOCUMENTS

| | | | | |
|---|---|---|---|---|
| 557,523 A | * | 3/1896 | Brown | 433/122 |
| 610,987 A | * | 9/1898 | Hendrickson et al. | 433/123 |
| 3,978,852 A | | 9/1976 | Annoni | |
| 4,235,253 A | * | 11/1980 | Moore | 132/322 |
| 4,455,138 A | * | 6/1984 | Sheridan | 433/3 |
| 4,880,382 A | * | 11/1989 | Moret et al. | 433/118 |
| 5,033,150 A | * | 7/1991 | Gross et al. | 15/22.1 |
| 5,189,751 A | | 3/1993 | Giuliani et al. | |
| 5,904,153 A | * | 5/1999 | Meibauer | 132/329 |

* cited by examiner

*Primary Examiner*—John J Wilson
(74) *Attorney, Agent, or Firm*—Neil John Graham

(57) ABSTRACT

The present invention is a powered instrument for removing excess bonding material from the surfaces of orthodontic brackets while they are attached to a patient's teeth. The instrument is particularly effective in removing bonding material from the inner surfaces of orthodontic bracket tie wings.

16 Claims, 6 Drawing Sheets

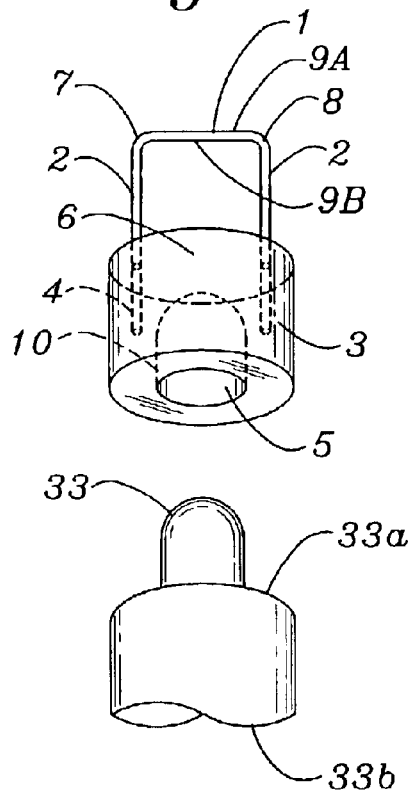
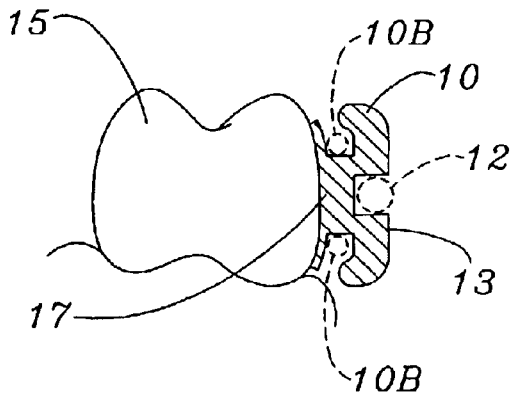
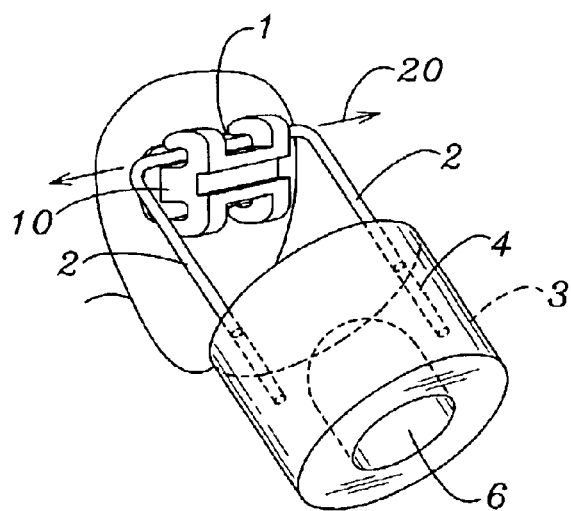
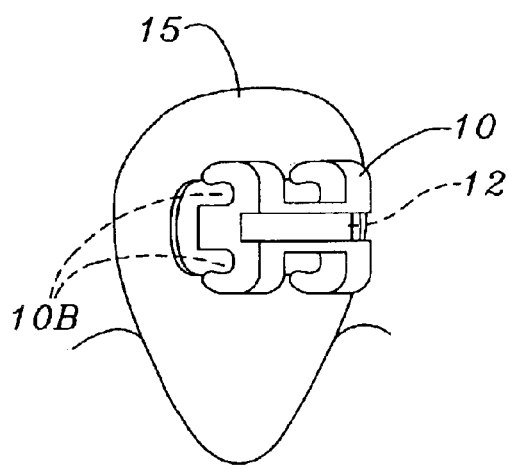

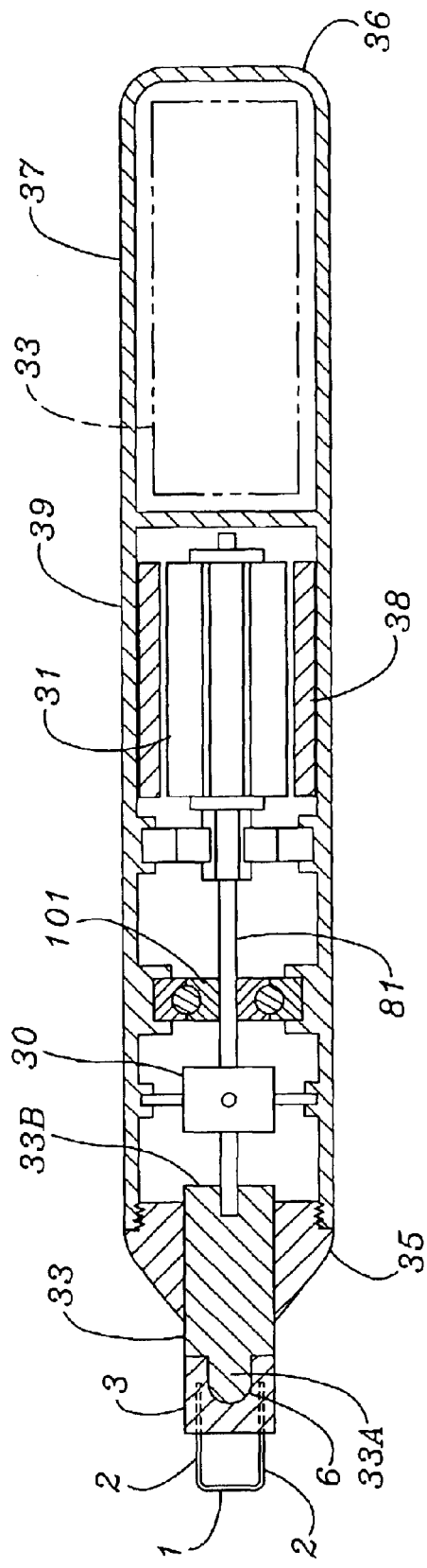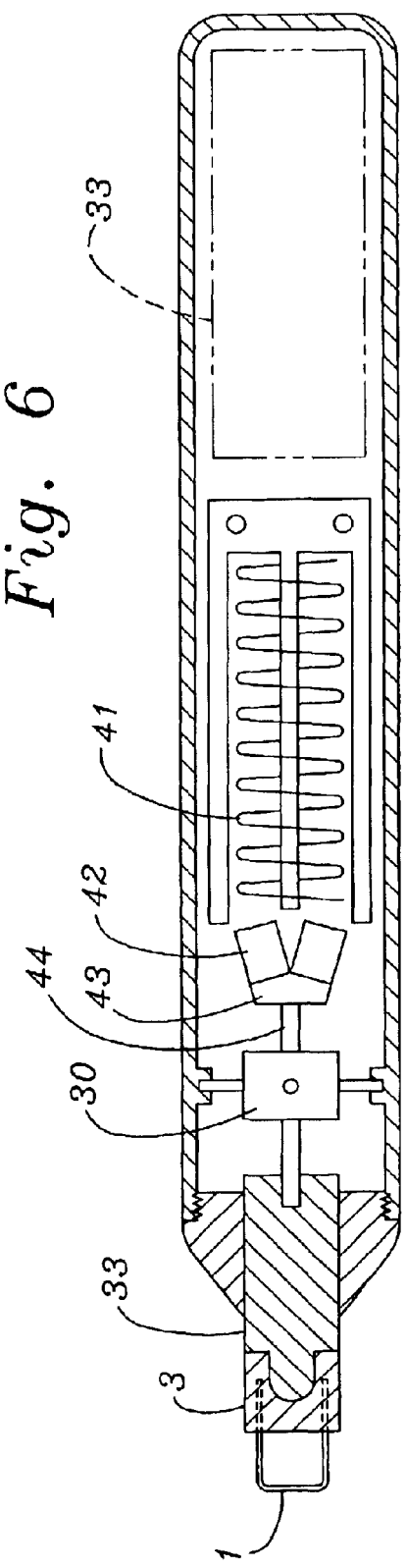

ORTHODONTIC BRACKET CLEANER

FIELD OF INVENTION

The present invention is directed to a devise for removing excess bonding material and cement from orthodontic brackets which are attached to a patient's teeth.

BACKGROUND OF THE INVENTION

Orthodontic procedures for straightening teeth involve attaching orthodontic brackets to a patent's teeth. In the past, the bracket was attached to an orthodontic band which was in turn cemented to the patient's tooth. Modernly, the orthodontic bracket has a mesh backing and is bonded adhesively directly to the patient's tooth. Orthodontic movement of the patient's teeth is accomplished by an orthodontic arch wire which is attached or ligated to the orthodontic bracket which transmits the force to the patient's teeth. The orthodontic bracket has a slot which receives the arch wire and bracket wings which allow the litigation of the wire to the bracket. The wings are basically hooks which extend toward surface of the teeth. During the bonding process the bonding material will occasionally lodge in the orthodontic bracket wing. The material must be removed in order to allow ligation of the arch wire to the bracket.

The removal of the bonding material has been attempted with dental instruments such as hand and power dental scalers and rotary dental drills. The difficulty is that the bonding material is difficult to visually see as it is on the tooth side of the orthodontic bracket wing and the gingival wing is often immediately adjacent to the patient's gingival tissue which further obstructed the view. Dental hand instruments are not particularly effective in removing the bonding material due to the strength and tenaciousness of the bonding material. A power dental drill could remove the material if it had access. The drill would have to be placed parallel to the surface of the tooth which the size and shape of the dental drill head prevents. When all fails the bracket has to be removed replaced, which is very time-consuming along with the difficulty of replacing the new bracket in the same position as the old bracket

SUMMARY OF THE INVENTION

In order to better understand the invention dental terminology should be explained. An orthodontic appliance consists of a series of orthodontic brackets attached to the patient's teeth. The following dental terminology is used: buccal is towards the patient's cheek; lingual is towards the tongue; gingival is towards the gums; anterior is towards a front of the mouth; posterior is towards the back of the mouth; incisors are the front teeth; molars and bicuspids are the back teeth; maxilla is the upper jaw; mandible is the lower jaw; and intermaxillary is between the jaws. A bracket has a central slot which receives an arch wire. The arch wire is the force Which actually aligns the teeth. The bracket has gingival and occiusal wings which are used to tie the arch wire to the bracket.

The present invention is directed to a device which removes excess bonding material from orthodontic brackets, more specifically the bracket tie wings. The orthodontic bracket cleaner comprises a U-shaped wire attached to a power means which moves the U-shaped wire in a single plane back and forth in the direction of the base of the U. The size requirement of the U-shaped wire is the wire must fully engage the inner hook areas of the occiusal and gingival tie wings. As the base portion is moved back and forth the bonding material is removed from the inner hook area allowing the bracket to be ligated. In a preferred embodiment the U-shaped wire is coated with diamond chips equivalent to a dental diamond drill, preferably graded to the coarse or extra coarse as used for dental drills. The back and forth motion of the U-shaped wire must be sufficiently rapid to quickly remove the bonding material. In another preferred embodiment the U-shaped wire 15 may be a spiral saw blade.

In another preferred embodiment the U-shaped wire may be a flat toothed saw blade where the cutting portion is angled towards the inner part of the bracket wings.

The U-shaped wire, in its preferred embodiment, is 0.018 in. to 0.020 in. in diameter and 6 mm. wide at its base. The diameter fits the inner hook surface of the tie wings and the width is enough to fit the width of brackets and narrow enough to not hit the adjacent teeth brackets when the U-shaped wire is in back and forth motion. The U-shaped wire is integrated into a female base which is removably attached to a male fitting which is attached to the means which converts to power means to a back and forth motion in a single plane. U.S. Pat. No. 3,978,852 to Annoni teaches a pivot arrangement in which a rotary power force is converted with a pivot arrangement to a single plane force. Another conversion of a rotary force to a back and forth single plane force is shown in No. 4 of the Dremel model 6000 contour sander internal schematic.

In a preferred embodiment the power means is a battery powered magnetic drive system as in U.S. Pat. No. 5,189, 751. One significant advantage of this magnetic drive system is that the drive unit may be physically separate from the U-shaped wire and force conversion portion; therefore, power loss due to mechanical linkages can be avoided. This power saving is very important in the charge life of a rechargeable battery powered unit. Power may also be provided from a 120 volt wall source.

In another preferred embodiment the power means may be a rotational armature driven motor, powered by a rechargeable battery or a 120 volt wall source.

In another preferred embodiment the power means may be a dental handpiece. The handpiece may be electrical or air driven.

BRIEF DESCRIPTION OF THE DRAWINGS

FIG. 1 is a perspective view of the removable longitudinal base wire-male base combination;

FIG. 2 is a cross section view of an orthodontic bracket mounted to a tooth;

FIG. 3 is a perspective view of an orthodontic bracket mounted to a tooth;

FIG. 4 is a view of the longitudinal base wire engaged in the inner surface of a bracket wing;

FIG. 5 is an internal view of a preferred embodiment of the orthodontic bracket cleaner;

FIG. 6 is an internal view of another preferred embodiment of the orthodontic bracket cleaner;

DETAILED DESCRIPTION OF THE INVENTION

Figure 7:
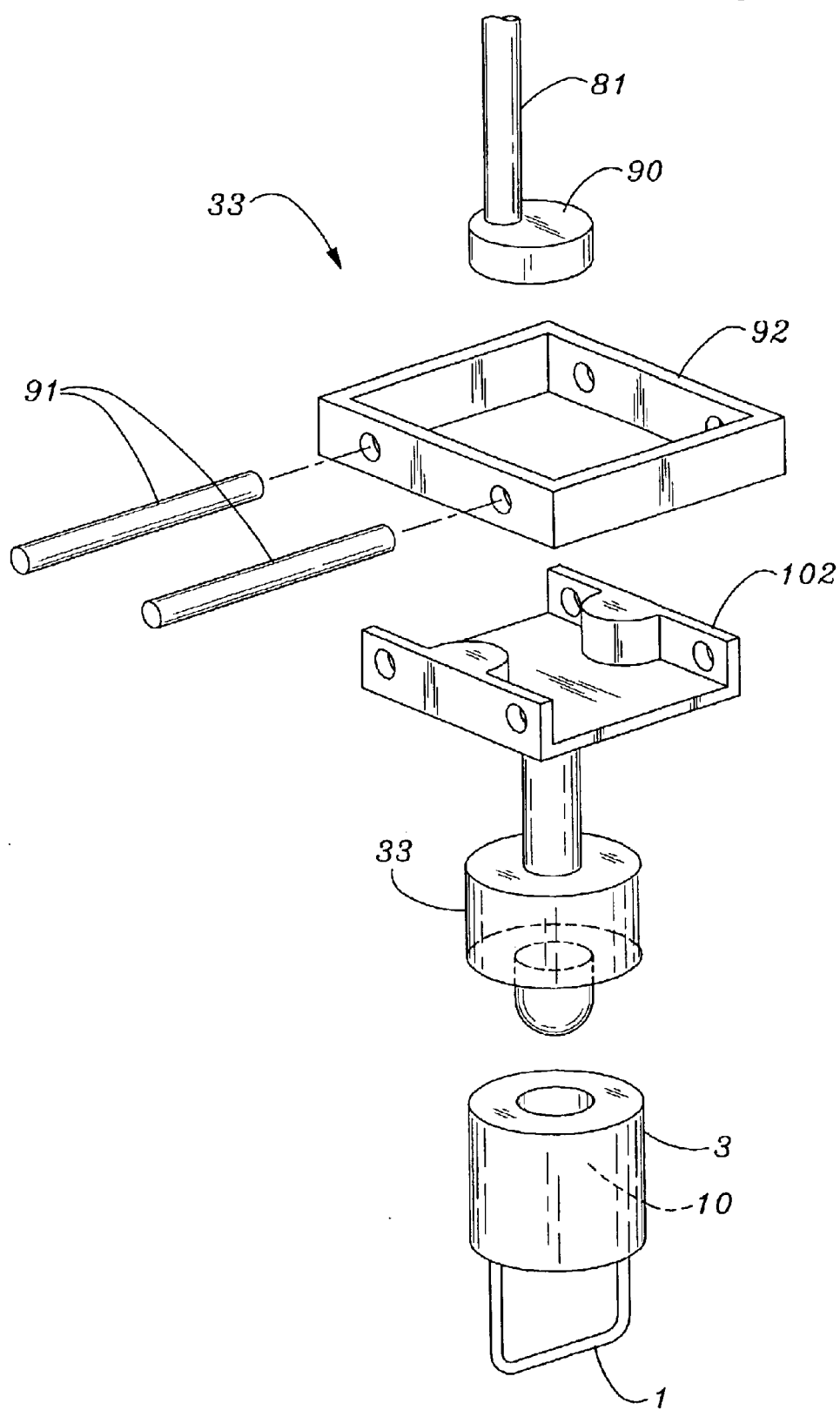
FIG. 7 is a view of the directional corrector.

Referring to FIG. 5 the orthodontic bracket cleaner has a longitudinal cylindrical body 39 with first 35 and second ends 36, an exterior 37 and an interior 38. In FIG. 6 a straight longitudinal base 1 extends beyond the first end 35 of the longitudinal cylindrical body 39. In FIG. 1 the longitudinal base 1 has a first 7 and second 8 end and a front 9A and back 9B side. In FIG. 1 a longitudinal side wire 2 extends from each end 7 and 8 of the longitudinal base wire 1 and away from the back side 9B of the horizontal base 1 and are parallel to each other. The two longitudinal side wires 2 are embedded into the solid first end 6 of a female base 3. The female base 3 has a first solid end 6 and a second open female end 5.

The wire longitudinal base 1 can have a diameter of 0.016–0.020 in. The preferred embodiment is 0.018–0.020 in. in diameter. This is thick enough to give the base rigidity and allow for a shape which conforms with the shape of the orthodontic bracket allowing the removal of the composite resins and cements from the surfaces of orthodontic brackets. The two longitudinal side wires 2 are continuous with the horizontal base 1 and comprising the same material as the base wire 1. In FIG. 5 a male fitting 33 is longitudinal in shape with a first end 35A and second end 35B, the first end 35B having a male fitting 33A. The male fitting 33 inserts into the female cavity 6, fitted tightly enough to prevent dislodging during use of the orthodontic bracket cleaner tool, but removable to allow replacement of the longitudinal wire base 1.

The female base 1 and the male fitting 33, in a preferred embodiment, are plastic in composition, such as, polyurethane, polypropylene or polyvinylchloride. A hard rubber-based composition may also be used. FIGS. 5,6,9 and 10.

In FIGS. 5 and 6 a power means 31 and 41 supplies a motion force to the male fitting 33 which is translated to movement of the longitudinal wire base 1. Intermediate between the power source 31 and 41 and its delivery to the male fitting 6 is a directional corrector 30 which translates the motion force into a horizontal force which moves the base wire 1 back and forth FIGS. 2 and 4 in the direction of its longitudinal axis when engaged in the wings 10B of the orthodontic bracket 10. Ideally the back and forth motion would be 2–3 mm in a straight line.

The orthodontic bracket cleaner is used intraorally to remove composite resins from orthodontic brackets. An orthodontic bracket FIGS. 2,3 and 4 is comprised of a base 17 bonded to a tooth 15. The central portion of the bracket 13 contains a bracket archwire slot 12, usually 0.018 in. or 0.022 in. for receiving an orthodontic archwire. Tie wings 10 extend occlusally and gingivally from the slot 12 with the inner tie areas 15 on the tooth side of the bracket wings 10 which are used to ligate the arch wire to the bracket 10. The inner part 10B of the bracket wing 10 is the most difficult area to remove excess material. The wire base 1 is placed in the inner hook area 10B, as in FIGS. 2 and 4, and is powered with sufficient frequency and torque to remove the material. In a preferred embodiment the width of the base wire 1 is 8 mm. This is enough width to simultaneously clean both wings of a twin bracket as in FIG. 4 and to allow for 2–3 mm of back and forth motion 20 of the wire. The orthodontic bracket cleaning tool in FIG. 5 in a preferred embodiment has as a power means an electrical armature rotary motor 31 powered by a battery 33 power source. The portability of battery power is desirable, but a 120 volt wall power source may also be used. In FIG. 5 the power shaft 81 is connected to a directional corrector 30 which transmits a back and forth motion force 20 to the wire base 1 via the male fitting 33 to female base 3. In FIG. 7 the direction corrector 30 is shown with an eccentric cam 61 and connected to the male fitting 33. This direction corrector is found in Dremel® tool model 8000.

Figure 8:
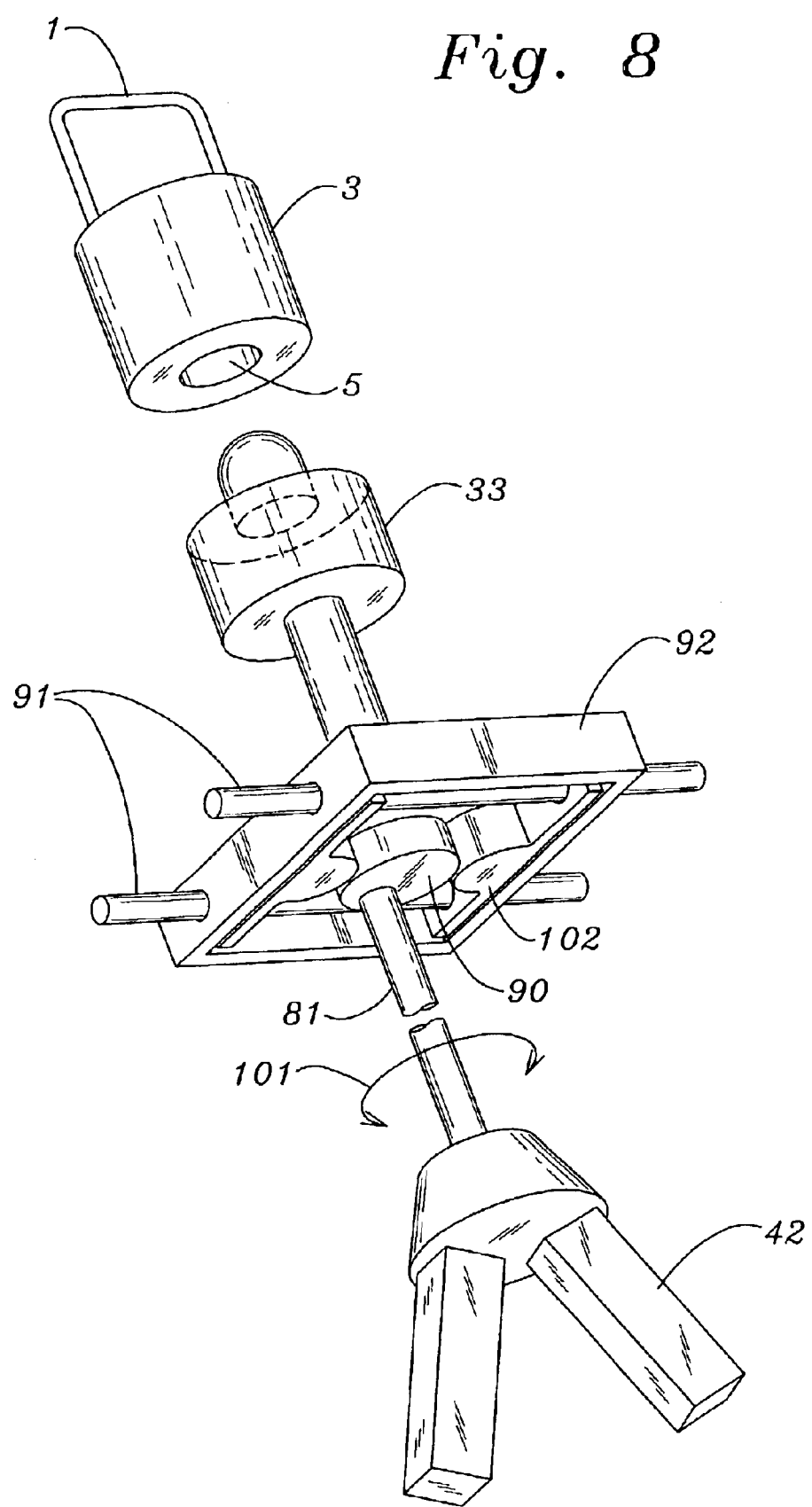
FIG. 8 is a view of the directional corrector as used with the electromagnetic power source.

Another preferred embodiment of the power means is shown in FIG. 6. This embodiment is found in U.S. Pat. No. 5,189,751 for a vibrating toothbrush. An electromagnet 41 receives an alternating current driving signal from an oscillating battery section 4. The frequency of operation is in the range of 150–400 Hz. A pair of permanent magnets 42 are provided at the end of a lever arm 44. The action of the alternating current in the electromagnet 41 upon the magnets 42 causes the lever arm 44 to move back and forth. The advantage of this power means is its energy efficiency due to the fact there is no mechanical connector between the electromagnetic and the magnets. A wall 120 volt power source may also be used. In FIG. 8 the force produced by the magnets 42 is a back and forth motion on a slight arc 101. In a preferred embodiment the power source is a battery where energy efficiency lengthens battery charge life.

Figure 9:
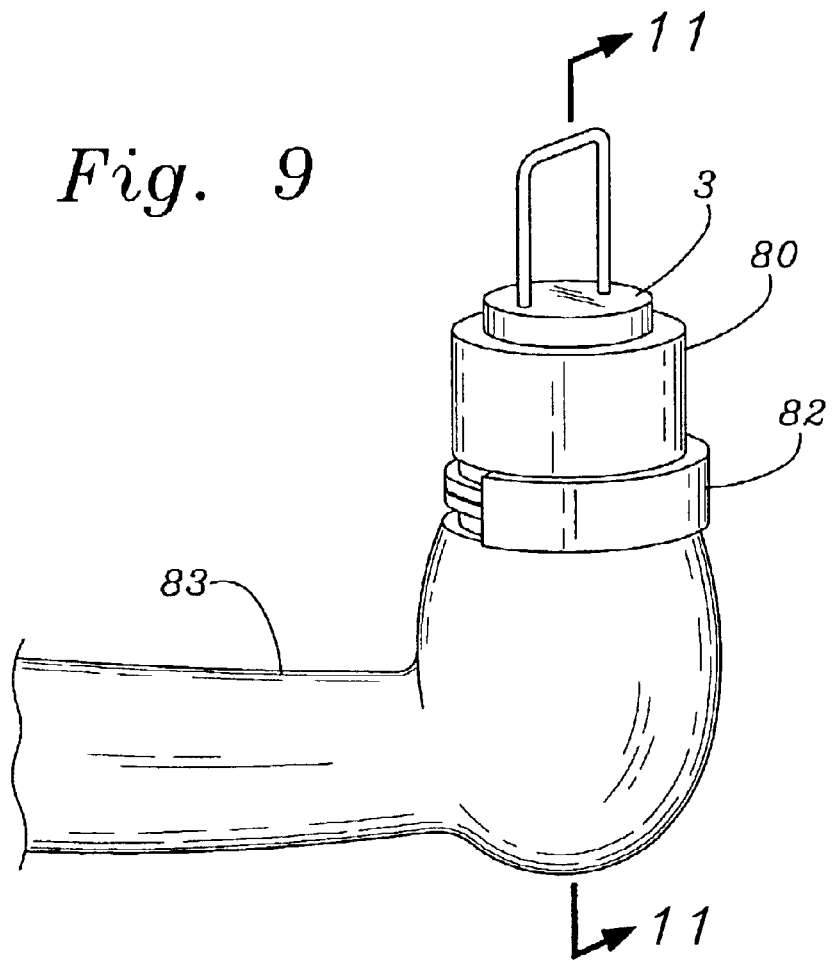
FIG. 9 is a view of a preferred embodiment of the orthodontic bracket cleaner adapted to a dental right angle handpiece.
Figure 10:
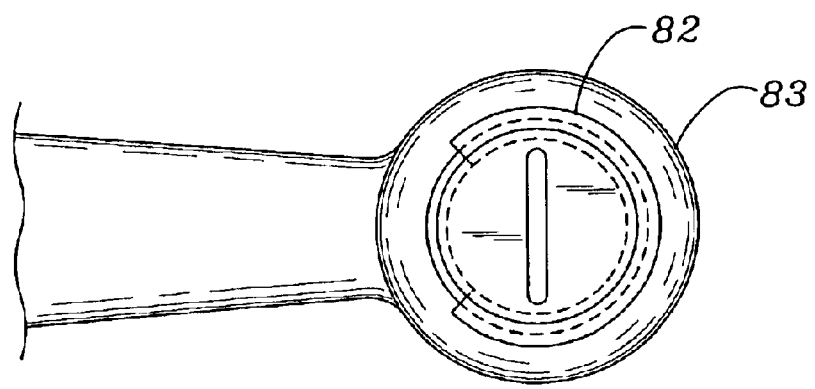
FIG. 10 is a view of the locking collar engaging the dental handpiece.
Figure 11:
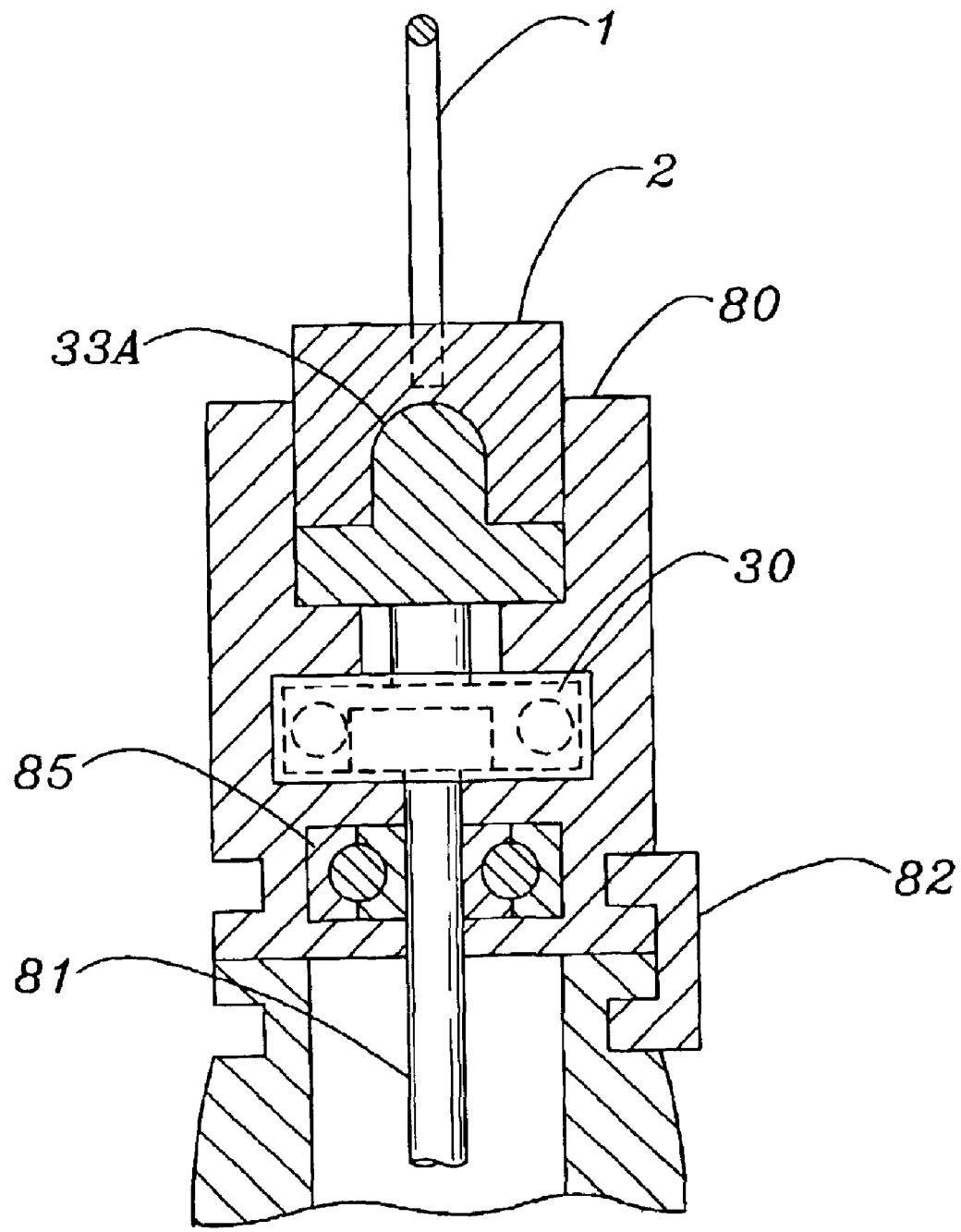
FIG. 11 is a cross section view of the handpiece embodiment.

In another preferred embodiment FIGS. 9, 10 and 11 the power means may be a dental handpiece 83. The handpiece may be electrical or air driven. The orthodontic bracket cleaner is in FIGS. 9, 10 and 11 wherein the orthodontic bracket cleaner is designed to fit a power means comprising a right angle handpiece 83, electrical or air driven. Referring to FIG. 11 the wire base 1 is attached to the two sides 2 which are embedded into the female base 3 which in turn connects via the male connector 33 to the directional corrector 30 The directional corrector 30 is the same as shown in FIG. 7. The directional corrector 30 is connected to a shaft 81 which is inserted and locked into the dental handpiece 83 as in FIG. 9. The orthodontic bracket cleaner mechanism is enclosed in a cylindrical housing 80 mounted to the shaft 81, as in FIG. 11, with a bearing means 85 mounting shaft 81 to the housing 80 wall. In FIGS. 9,10 and 11 a collar 82 is shown at the handpiece end of the cylindrical housing 80 which encircles the head of the handpiece 83 preventing the entire cylindrical housing 80 from rotating during operation.

The handpiece mounted orthodontic bracket cleaner FIGS. 9, 10, 11 is also adaptable to a straight dental handpiece.

The preferred embodiment of the directional corrector 30 used in all the embodiments involving a rotational power source is shown in FIGS. 7 and 8. The shaft 81 from the power source has an eccentric lobe 90 at its end. The lobe 90 as it rotates strikes cams on the internal moving mount 94 which is mounted on two rings 91 to a pin anchor housing 92, producing a straight line back and forth horizontal movement which is translated directly to the wire base 1 by way of the male fitting 33, the female base 3, and the two sides 2.

I claim:

1. An orthodontic bracket cleaner for removing excess material from orthodontic brackets comprising:
   a hollow cylindrical body with a first open end and a second closed end and an exterior and an interior;
   a longitudinal base having opposing first and second ends, a front side and a back side, and a longitudinal axis wherein the longitudinal base is wire and coated with diamond chips producing an abrasive surface for removing cementing materials from orthodontic brackets;
   two longitudinal sides with first and second ends wherein the first ends are attached each to an opposing end of the longitudinal base and extending at right angles to the longitudinal base away from the back side of the longitudinal base and parallel to each other;
   a cylindrical female base with first and second ends and an internal cavity, the first end facing the longitudinal base and attached to the second ends of the longitudinal sides, the second cylindrical female base end, facing away from the longitudinal base, defines the internal cavity extending 2–4 mm into the cylindrical female base interior, wherein the longitudinal base, longitudinal sides, and cylindrical female base form an integral replaceable unit;
   a cylindrical male fitting with first and second ends, the first end with a male extension sized to removably fit within the internal cavity at the second end of the cylindrical female base, wherein the cylindrical male fitting is enclosed within the first end of the cylindrical body;
   an apparatus means for redirecting force wherein the apparatus means has first and second apparatus ends which converts a motion force into a linear back and forth force moving the longitudinal base back and forth in its long axis, wherein the first apparatus end is connected to the second end of the cylindrical male fitting;
   a force-producing means apparatus positioned internally in the body for producing a motion force, wherein the force-producing apparatus applies a motion force to the second end of the force direction corrector apparatus; and
   a power source means for supplying electrical power to the force-producing apparatus wherein the power source is located in the interior of the cylindrical body at the second end.

2. An orthodontic bracket cleaner as in claim 1 wherein the longitudinal base is 6 mm in length allowing bath bracket wings of a twin orthodontic bracket to be cleaned simultaneously.

3. An orthodontic bracket cleaner as in claim 1 wherein the longitudinal base has a diameter of 0.018 in. allowing the bracket slots of the orthodontic bracket to be cleaned as well as the orthodontic bracket wing.

4. An orthodontic bracket cleaner as in claim 1 wherein the apparatus means for re-directing force produces a straight line linear force which moves the longitudinal base back and forth in its longitudinal axis 2–3 mm producing a sanding effect upon the excess cementing material.

5. An orthodontic bracket cleaner as in claim 1 wherein the power source means is a 120 AC wall power source.

6. An orthodontic bracket cleaner as in claim 1 wherein the power source means source is a battery.

7. An orthodontic bracket cleaner for removing excess cementing materials from orthodontic brackets comprising:
   a hollow cylindrical body with first and second ends and an exterior and an interior and a diameter of approximately 1.2 in;
   a longitudinal base with opposing first and second ends, a front side and a back side, and a longitudinal axis wherein the longitudinal base is a spiral saw blade 0.014–0.020 inch in diameter;
   two longitudinal sides with first and second ends wherein the first ends are attached each to an opposing end of the longitudinal base and extending at right angles to the longitudinal base away from the backside of the longitudinal base parallel to each other;
   a cylindrical female base with first and second ends and an internal cavity, the first end facing the longitudinal base and attached to the second ends of the longitudinal sides wherein the second cylindrical female base end, facing away from the longitudinal base defines the internal cavity extending 2–4 mm into the cylindrical female base interior;
   a cylindrical male fitting with first and second ends wherein the first end has a male extension sized to removably fit the cylindrical female base allowing the longitudinal base, longitudinal sides and cylindrical female base combination to be with exchanged with a new combination;
   an apparatus means for redirecting force wherein the apparatus means has first and second ends which converts a motion force into a linear back and forth force moving the longitudinal base back and forth in its long axis, wherein the first apparatus end is connected to the second end of the cylindrical male fitting and enclosed in the interior of the cylindrical body;
   a force producing means apparatus positioned internally in the body wherein the force producing means is a magnetic drive system located adjacent to and delivers a motion force to the second end of the force direction corrector;
   a power source means for supplying electrical power to the force- producing apparatus wherein the power source is located in the interior of the cylindrical body at the second end; and
   a means for mounting the cylindrical male fitting and the force direction corrector, wherein a flexible material is used which will allow the back and forth movement of the longitudinal base .

8. An orthodontic bracket cleaner as in claim 7 wherein the power source means is a disposable rechargeable battery.

9. An orthodontic bracket cleaner as in claim 7 wherein an electrical switch means is mounted to the exterior of the body for turning the turning the power on and off.

10. An orthodontic bracket cleaner as in claim 7 wherein a variable power switch means for varying the speed of the orthodontic bracket cleaner is mounted on the exterior wall of the cylindrical body.

11. An orthodontic bracket cleaner for removing excess cementing materials from orthodontic brackets comprising:

a cylindrical body with first and second ends and an exterior and an interior;

a longitudinal base having opposing first and second ends, a front side and a back side, and a longitudinal axis wherein the longitudinal base is metal and coated with diamond chips with a diameter of 0.014–0.020 inch, two longitudinal sides with first and second ends wherein the first ends are attached each to an opposing end of the longitudinal base and extending at right angles to the longitudinal base away from the back side of the longitudinal base parallel to each other;

a cylindrical female base with first and second ends and an internal cavity, the first end facing the horizontal base and attached to the second ends of the longitudinal sides wherein the second end, facing away from the longitudinal base, defines the internal cavity extending 2–4 mm into the cylindrical base interior;

a cylindrical male fitting with first and second ends, the first end with a male extension sized to removably fit with the female cavity of the cylindrical female base;

means force direction corrector apparatus which converts the force from the force-producing apparatus to a linear back and forth force which is transmitted to the second end of the cylindrical male base;

a means for producing force apparatus in the interior of the body for producing a motion force;

a cylindrical longitudinal metal shaft extending from the second end of the male base, the shaft being the same length and diameter as a dental drill shaft for mounting into a dental handpiece; and a power source means for using an electrical or air driven dental handpiece wherein the dental handpiece has a female adjustable chuck and the cylindrical longitudinal shaft extending from the male fitting is secured within the handpiece chuck.

12. An orthodontic bracket cleaner as in claim 11 wherein the longitudinal base movement is back and forth 3–4 mm upon the long axis of the horizontal base.

13. An orthodontic bracket cleaner as in claim 11 wherein a locking collar encircles the handpiece head and is attached to the second end of the cylindrical housing preventing rotation of the bracket cleaner during operation of the dental handpiece.

14. An orthodontic bracket cleaner as in claim 11 wherein the horizontal base is a metal spiral file 0.014–0.020 inch in diameter in its longitudinal base.

15. An orthodontic bracket cleaner as in claim 11 wherein the female base, male fitting, and the cylindrical shaft are mounted to the cylindrical body with ball bearing means permitting rotation within the cylindrical body interior.

16. An orthodontic bracket cleaner as in claim 11 wherein the male extension of the cylindrical male fitting projects from the first end of the cylindrical body and a flexible seal means such as a rubber cone connects from the exterior of the cylindrical body to the cylindrical male fitting body wherein a seal is formed protecting the interior of the cylindrical body from moisture and debris and allows movement of the horizontal base.

* * * * *